AVOCADO TREE

Filed March 28, 1974 2 Sheets-Sheet 1

United States Patent

Plant Pat. 3,712
Patented Apr. 29, 1975

3,712

AVOCADO TREE

John Pinkerton, 10681 Foothill Road, Ventura, Calif. 93003

Filed Mar. 28, 1974, Ser. No. 456,071
Int. Cl. A01h *5/03*
U.S. Cl. Plt.—44 1 Claim

ABSTRACT OF THE DISCLOSURE

The new avocado tree is characterized by a relatively small seed and longer shelf life relative to ordinary Fuerte avocados, and further bears fruit annually.

This invention relates to a new and distinct variety of avocado tree and is characterized as to primary novelty by a small seed and longer shelf life relative to ordinary Fuerte avocados and heavy bearing annually.

The novel avocado tree results from a seedling discovered near a tree of the Hass variety in Coyote Ranch, Ventura, Calif. I have reproduced the tree by budding and grafting it to an Anaheim tree. The asexual reproduction of the instant variety of avocado tree by budding or grafting has resulted in substantially superior avocados of smaller seed and longer shelf life than a conventional Fuerte avocado. Observations of the new tree may be made at the Pinkerton Ranch office, off Foothill in Ventura, Calif.

Figure 1:
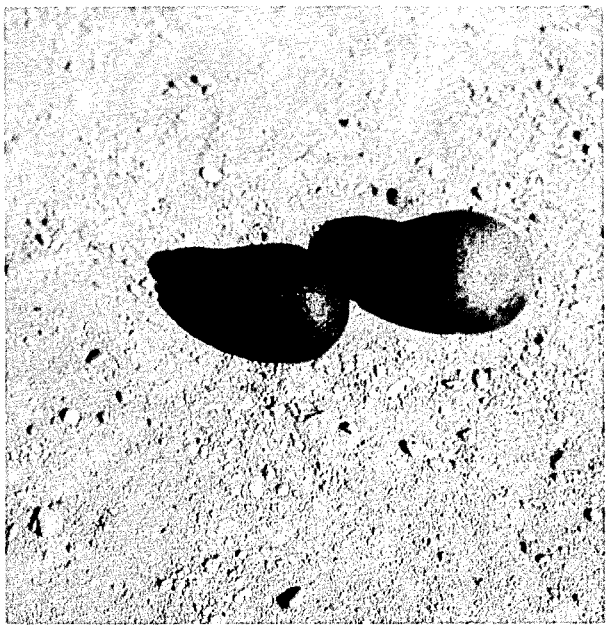

In FIG. 1 of the accompanying drawings, there is shown the new and distinct variety of avocado to the left compared to a conventional Fuerte avocado. The skin of the new avocado is leathery and does not bruise easily. Further, it takes a relatively longer time to soften, close to a month. As a consequence, shipping quality and long shelf life are improved. The Fuerte softens sooner and bruises more easily.

Figure 2:
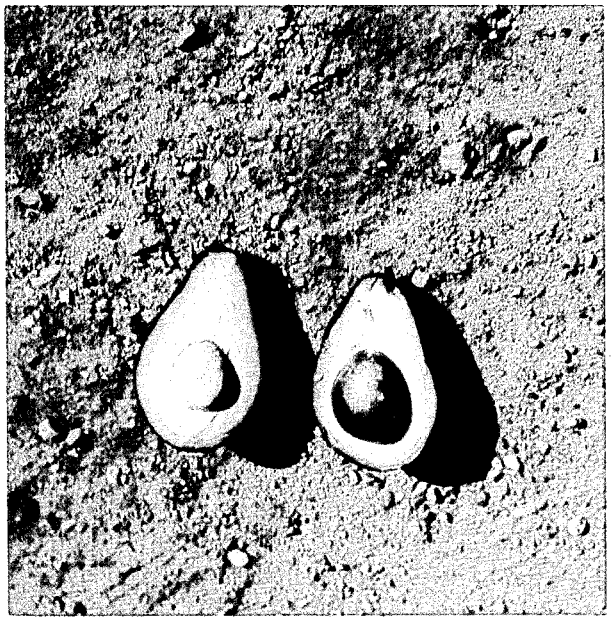

FIG. 2 of the accompanying drawings shows the new avocado on the left compared to the conventional Fuerte avocado on the right in cross section, wherein it will be noted that the avocado of the present invention has a substantially smaller seed.

Figure 3:
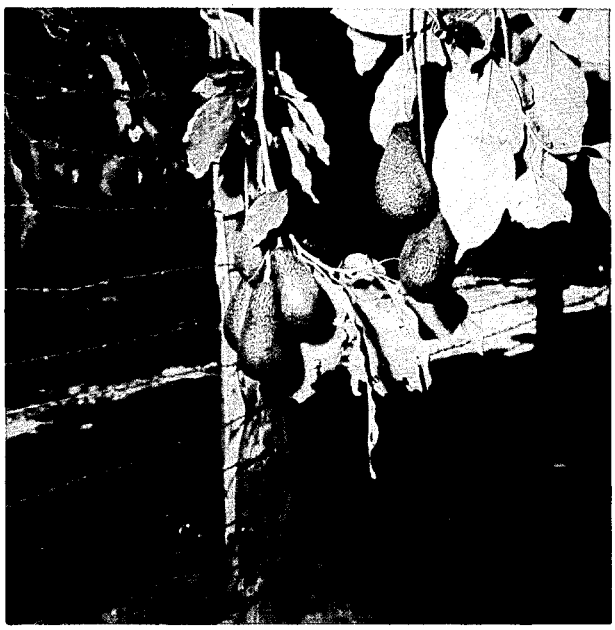

In FIG. 3, there is shown a typical cluster of the new and distinct variety of avocado of this invention. Also illustrated is the foliage or leaves.

Following is an outline description in greater detail of the distinct variety of the avocado tree of this invention:

PLANT

Form: Normal spreading tree.
Growth: Vigorous.
Wood:
*New wood.*—Color—dark green. Bark—smooth.
*Old wood.*—Color—brown. Bark—smooth.
Foliage: Single leaf.
*Size.*—Normal.
*Quantity.*—Abundant.

*Color.*—New foliage: Upper side—dark green; underside—light green. Old foliage: Upper side—dark green; under side—light green.
*Shape.*—Oval, pointed.
*Texture.*—Upper side—very smooth. Under side—smooth.
*Ribs and veins.*—Ordinary.
*Edge.*—Smooth.
*Leaf stem color.*—Light green.
Fruit: Excellent quality. Grows in heavy clusters, annually. Skin peels readily.
*Form.*—Pear shaped.
*Aspect.*—Leathery.
*Color at maturity.*—Skin and flesh similar to Fuerte.
*Size at maturity.*—Length and width generally similar to Fuerte.
*Seed.*—Very small, from ½ to ⅔ that of Fuerte.
Blooming habit: Long blooming period from February to April annually.
Bearing habit: December to May.

The most distinguishing characteristic of the fruit is its small seed and long shelf life relative to the conventional Fuerte avocado and also its heavy bearing on an annual basis.

The State law of California requires that avocados contain at least eight percent (8%) oil. The following table indicates that the present distinct variety of avocado generously exceeds this minimum when it is mature.

Two small, two medium and two large avocados of the present invention were picked and the oil content of each is set forth:

| Weight in ounces: | Oil content, percent |
|---|---|
| 6¼ | 10.1 |
| 6½ | 10.9 |
| 10 | 13.0 |
| 10¼ | 12.3 |
| 15¾ | 20.6 |
| 16 | 22.0 |

In addition to all of the foregoing characteristics set forth, the new avocado has an excellent taste and provides more fruit becauses of the smaller seed.

The avocado tree and its fruit as described herein may vary in slight detail due to climate or soil conditions under which the variety is grown.

What is claimed is:

1. A new and distinct variety of avocado substantially as shown and described, characterized particularly as to novelty by the unique combination of a small seed and longer shelf life relative to ordinary Fuerte avocados, and heavy bearing annually.

No references cited.

ROBERT E. BAGWILL, Primary Examiner